United States Patent
Thorley

(10) Patent No.: US 8,790,313 B2
(45) Date of Patent: Jul. 29, 2014

(54) SYRINGE ADAPTER

(75) Inventor: Craig Stephen Thorley, Largs (AU)

(73) Assignee: Unitract Syringe Pty Ltd, Syndey (AU)

( * ) Notice: Subject to any disclaimer, the term of this patent is extended or adjusted under 35 U.S.C. 154(b) by 203 days.

(21) Appl. No.: 13/378,030

(22) PCT Filed: Jun. 16, 2010

(86) PCT No.: PCT/AU2010/000743
§ 371 (c)(1),
(2), (4) Date: Feb. 1, 2012

(87) PCT Pub. No.: WO2010/144957
PCT Pub. Date: Dec. 23, 2010

(65) Prior Publication Data
US 2012/0130317 A1    May 24, 2012

(30) Foreign Application Priority Data
Jun. 17, 2009   (AU) ................ 2009902776

(51) Int. Cl.
*A61M 5/31* (2006.01)
*A61J 1/20* (2006.01)
*A61M 5/32* (2006.01)

(52) U.S. Cl.
CPC *A61J 1/20* (2013.01); *A61J 1/2089* (2013.01); *A61J 2001/2086* (2013.01); *A61M 2005/3114* (2013.01); *A61M 5/3202* (2013.01); *Y10S 604/905* (2013.01)
USPC ............ 604/192; 604/190; 604/187; 604/905

(58) Field of Classification Search
CPC .............. A61M 2005/3114; A61M 2005/3202; A61M 2005/3213; A61J 1/00; A61J 1/20; A61J 1/2089; A61J 1/2096
USPC .......... 604/181, 187, 190, 192, 198, 263, 905
See application file for complete search history.

(56) References Cited

U.S. PATENT DOCUMENTS 4,728,320 A * 3/1988 Chen ............................ 604/110
5,125,415 A    6/1992 Bell
(Continued)

FOREIGN PATENT DOCUMENTS

GB    847913    9/1960
GB    1375675   11/1974
(Continued)

OTHER PUBLICATIONS

Australian Patent Office, International Search Report in International Patent Application No. PCT/AU2010/000743 (Jul. 29, 2010).

*Primary Examiner* — Laura Bouchelle
(74) *Attorney, Agent, or Firm* — Leydig, Voit & Mayer, Ltd.

(57) ABSTRACT

A syringe adapter mountable to a syringe, particularly a retractable syringe having a retractable needle, comprises a sealing member and an adapter body that comprises two or more body members that co-operate to retain the sealing member in the adapter. One or the other body members is removably mountable to a barrel of the syringe and one or the other body members comprises a mounting member. A filter member may be removably mounted to, or formed integrally with, the mounting member to filters fluid when filling the syringe to thereby remove particular material, impurities or the like. Alternatively, a filter material may be provided in the syringe adapter. In addition, or alternatively, a filling needle is provided which is removably mountable to the syringe adapter and may prevent bending or burring of the retractable needle.

17 Claims, 5 Drawing Sheets

(56) References Cited

U.S. PATENT DOCUMENTS

| | | | |
|---|---|---|---|
| 5,147,309 A * | 9/1992 | Hemmerich et al. | 604/122 |
| 6,083,199 A | 7/2000 | Thorley et al. | |
| 6,524,278 B1 | 2/2003 | Campbell et al. | |
| 2003/0236501 A1 * | 12/2003 | Donnan et al. | 604/192 |

FOREIGN PATENT DOCUMENTS

| | | |
|---|---|---|
| WO | 01/80930 A1 | 11/2001 |
| WO | 03/061735 A1 | 7/2003 |
| WO | 2004/082747 A1 | 9/2004 |
| WO | 2006/064231 A1 | 6/2006 |

\* cited by examiner

SYRINGE ADAPTER

FIELD

THIS INVENTION relates to syringes. More particularly, this invention relates to an adapter for a syringe which facilitates removably mounting or attaching a filter or filling needle to the syringe. Even more particularly, the syringe is a retractable syringe.

BACKGROUND

The practice of sharing and re-using syringes without adequate sterilization between successive users is a major contributor to the transfer of Human Immunodeficiency Virus (HIV) and Hepatitis with subsequent severe repercussions for the sufferer and at a high cost to society for supporting and providing medical attention to sufferers. Furthermore, health professionals may be exposed to used syringes which can lead to inadvertent needlestick injuries and possible exposure to infective pathogens or other contaminants.

One solution to these problems has been the introduction of single-use syringes for use in hospitals, medical centres and vaccination programs and also for use by intravenous drug users. However, such syringes typically comprise a specialized barrel and/or needle assembly (e.g. a retractable needle assembly) which are not readily amenable to modification or adaptation to allow filtering of injectable fluids during filling of the syringe or to replace bent or burred needles.

With particular regard to the need for filtering, an injectable substance may include potentially dangerous impurities such as particulate material that can cause abscesses, oedema and/or embolism in a user. Because some injectable drugs may be obtained illicitly, the purity and quality of the injectable drug is often poor. This is particularly a problem with drugs of addiction such as heroin, which may be due to impurities in the drug itself, or in substances combined with the drug to improve injectability. To address this problem a filter may be used with the syringe to ensure that fluid withdrawn into the syringe through the filter is rendered free of particulate matter and other impurities. An example of such a filter is the Sterifilt™ filter produced by Apothicom. In some countries this is a legal requirement of needle exchange programs for intravenous drug users.

SUMMARY

It is accordingly an object of the invention to ameliorate one or more problems of the prior art, or to at least provide a useful alternative.

With this in mind, the present invention provides a syringe adapter mountable to a syringe. Suitably, the adepter facilitates mounting of a filter to the syringe and/or mounting a filling needle to the syringe.

Typically, the syringe comprises a needle or needle assembly that is not replaceable or interchangeable by another needle or needle assembly.

Preferably, the syringe is a retractable or single-use syringe comprising a retractable needle or needle assembly.

In a first aspect, the invention provides a syringe adapter mountable to a syringe, said adapter comprising: (i) a sealing member penetrable by a needle of said retractable syringe; and (ii) an adapter body comprising two or more members that co-operate to retain the sealing member in the adapter, at least one of which members is capable of being mounted to a barrel of said syringe and wherein at least one of which members comprises a mounting member.

Preferably, the syringe adapter is removably mountable to the syringe.

Preferably, the two or more members comprise a barrel member. Suitably, the barrel member is mountable to the barrel of said syringe.

In one embodiment, the two or more members further comprise an outer member. According to this embodiment, preferably the barrel member and the outer member co-operate to retain the sealing member in said adapter. Suitably, the outer member comprises the mounting member.

In another embodiment, the two or more members further comprise a retaining member. According to this embodiment, the retaining member cooperates with the barrel member to retain the sealing member in said adapter. Preferably, according to this embodiment, the barrel member comprises the mounting member.

In one particular embodiment, the mounting member comprises a luer.

In another particular embodiment, the mounting member comprises a filter material therein.

In yet another particular embodiment, the mounting member comprises a filter member mounted thereto. Preferably, the filter member is removably mounted to the mounting member. Alternatively, the filter member is integrally formed with the mounting member.

In another alternative embodiment, the mounting member comprises a filling needle removably mounted thereto.

In another aspect, the invention provides a syringe comprising the syringe adapter of the aforementioned aspect mounted thereto.

Preferably, the syringe adapter is removably mounted thereto.

In yet another aspect, the invention provides a method of filling the syringe of the aforementioned aspect, said method including the step of operating the syringe to fill the syringe with fluid contents.

Preferably, the method further includes the step of mounting the syringe adapter to the retractable syringe before operating the syringe to fill the syringe with fluid contents.

Preferably, the method further includes the step of removing the syringe adapter from the retractable syringe after operating the syringe to fill the syringe with fluid contents.

It is preferred that the syringe according to the aforementioned aspects is a retractable syringe that comprises a retractable needle and/or needle assembly.

Throughout this specification, unless otherwise indicated, "comprise", "comprises" and "comprising" are used inclusively rather than exclusively, so that a stated integer or group of integers may include one or more other non-stated integers or groups of integers.

BRIEF DESCRIPTION OF THE DRAWINGS

Non-limiting embodiments of the invention are described herein with reference to the following drawings wherein.

DETAILED DESCRIPTION

The syringe adapter described in detail herein is described with particular reference to a retractable syringe such as described in U.S. Pat. No. 6,083,199, International Publication WO01/80930 and/or International Publication WO2004/082747. A retractable syringe of this type typically comprises a barrel; a plunger capable of axial movement within the barrel to facilitate filling and delivery of fluid contents; and a retractable needle which couples with the plunger to facilitate needle retraction under the influence of spring decompression. However, it will be appreciated from the following detailed description that the inventive principle set forth herein can be practiced with any syringe, retractable or otherwise, with minimal modification required on the part of the skilled person.

Figure 1:
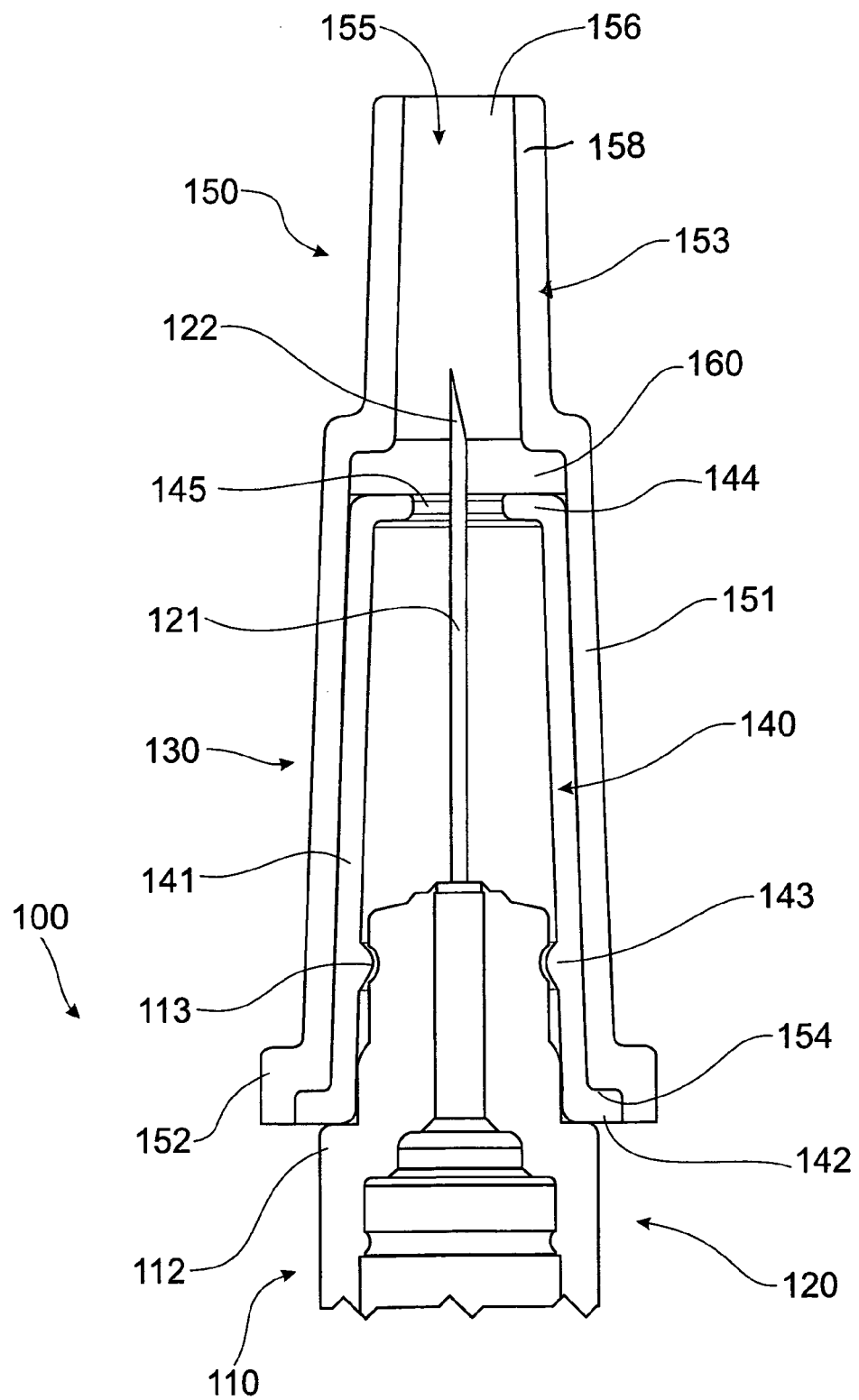
FIG. 1 is a sectional view of an embodiment of a syringe comprising a syringe adapter removably mounted thereto.

Referring to FIG. 1, syringe 100 comprises barrel 110, retractable needle assembly 120 comprising cannula 121 having beveled inlet 122 and syringe adapter 130. Syringe adapter 130 comprises barrel member 140 and outer member 150. Barrel member 140 comprises body portion 141 and base flange 142 that releasably engages rim 112 of barrel 110. Barrel member 140 further comprises circumferential rib 143 that releasably engages complementary circumferential groove 113 in barrel 110. Barrel member 140 further comprises crown 144 having cannula aperture 145. Outer member 150 comprises body portion 151, filter aperture 156, base rim 152, mounting member 153 comprising luer taper 158 and inner circumferential shoulder 154. Both body portion 141 and body 151 are substantially frusto-conical in shape. However, other complementary shapes or configurations may be used which allow barrel member 140 and outer member 150 to co-operatively form syringe adapter 130.

Barrel member 140 and outer member 150 are typically glued or otherwise adhered together to form syringe adapter 130.

Inner circumferential shoulder 154 and crown 144 co-operate to retain sealing member 160 in place. Sealing member may be made of any flexible or resiliently deformable, water-resistant material, such as rubber. Sealing member 160 effectively defines a fluid reservoir in void 155. In this embodiment, sealing member 160 is held in particular relation to beveled inlet 122 of cannula 121 which pierces sealing member 160 so that there is an uninhibited flow of fluid through cannula 121 into barrel 110 when drawing fluid into syringe 100, while minimizing "dead space" in void 155 of luer 153. This maximizes the efficiency of fluid transfer into barrel 110 by leaving minimal residual fluid retained in void 155 of mounting member 153.

Figure 2:
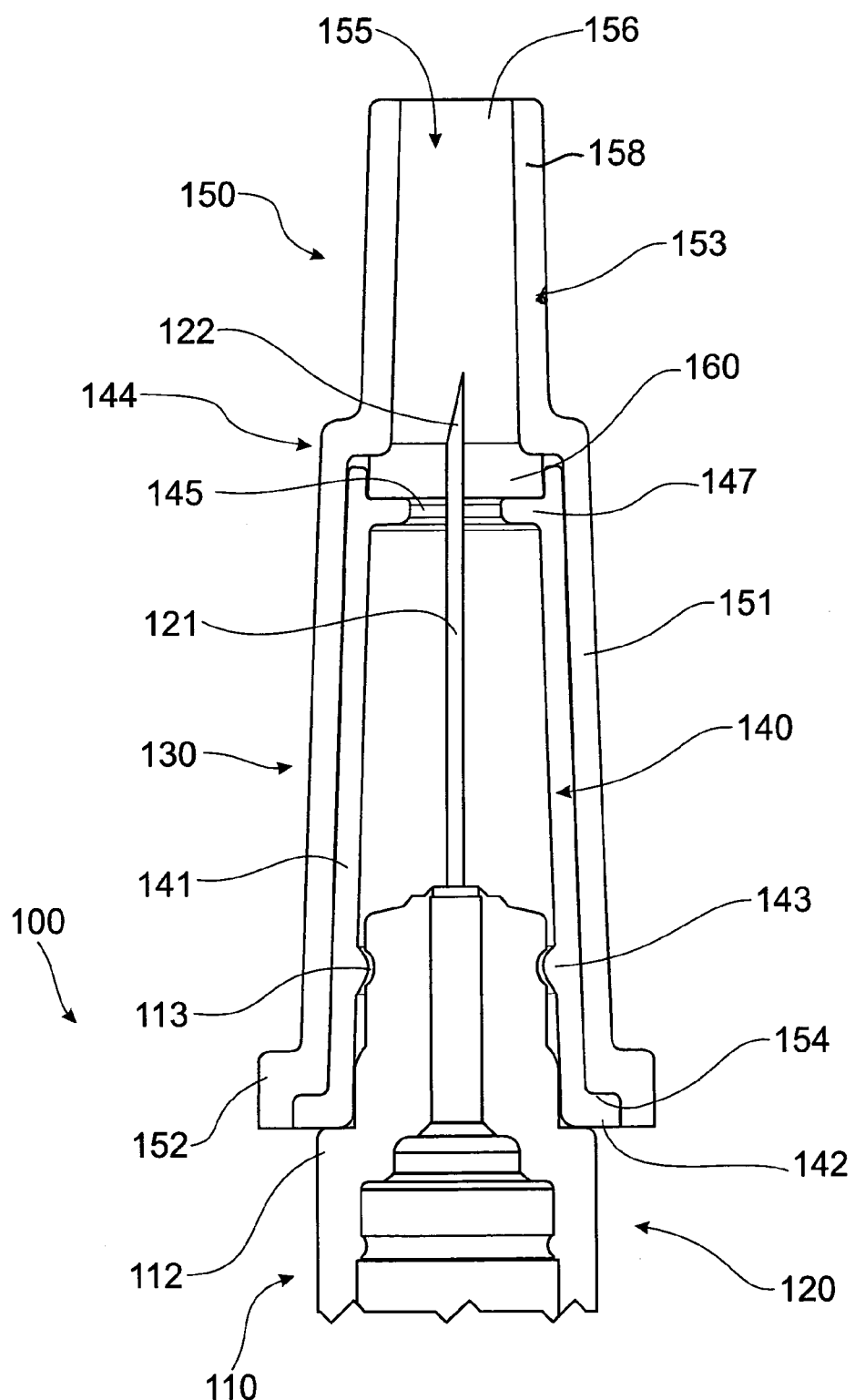
FIG. 2 is a sectional view of another embodiment of a syringe comprising a syringe adapter removably mounted thereto.

In another embodiment shown in FIG. 2, crown 144 of barrel member 140 comprises circumferential seat 147 that accommodates sealing member 160 bearing against inner circumferential shoulder 154.

Figure 3:
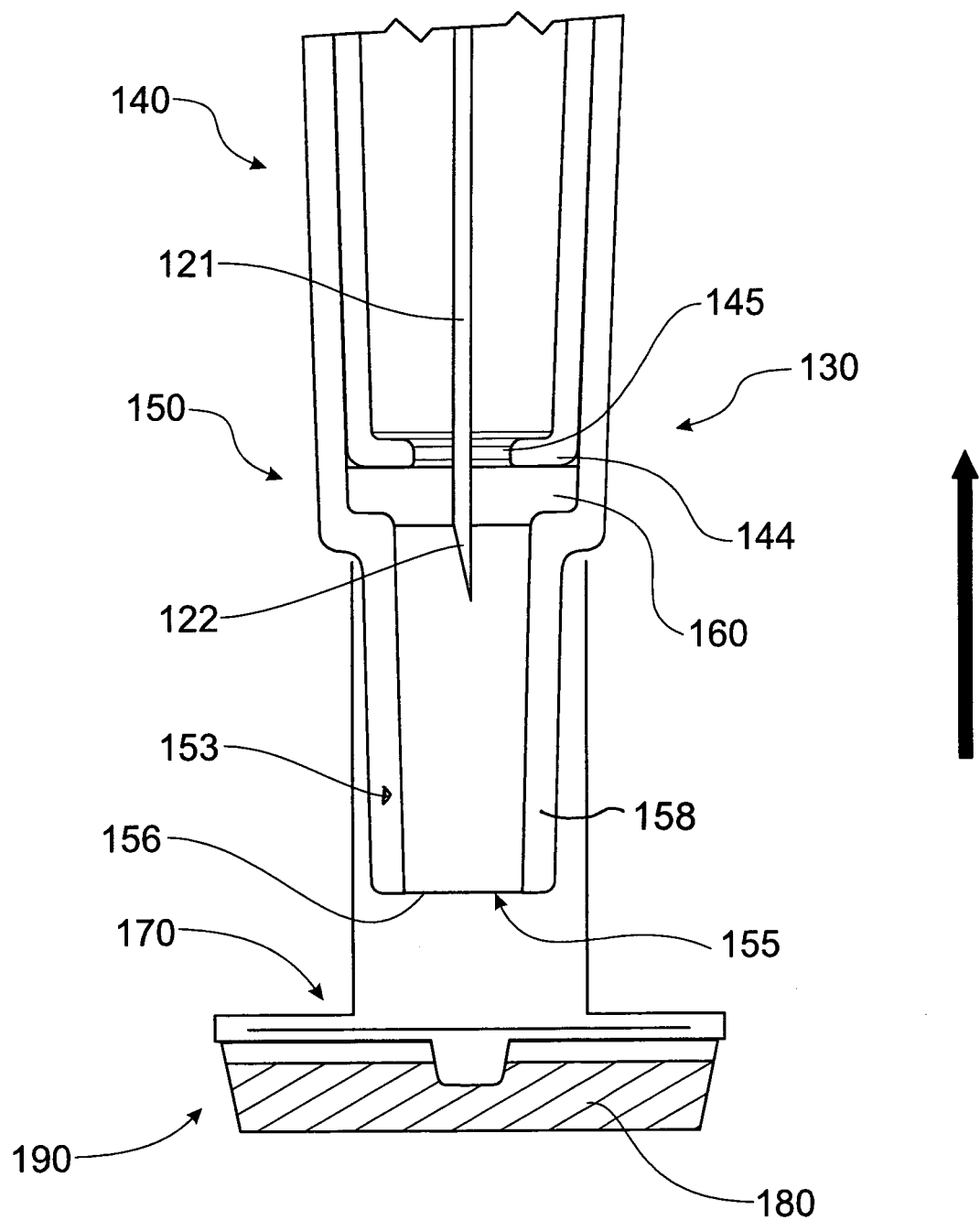
FIG. 3 is a sectional view of an embodiment of a syringe comprising a syringe adapter with a filter removably mounted thereto.

With reference to FIG. 3, filter 170 is removably mounted to the embodiment of syringe adapter 130 shown in FIG. 1, which is removably mounted to syringe 100. In use, withdrawal of a syringe plunger (not shown) in the direction of the solid arrow draws injectable fluid 180 from vessel 200 through filter 170 into void 155 of syringe adapter 130, thereby filtering the injectable fluid 180. The filtered, injectable fluid 180 then enters cannula 121 through beveled inlet 122 to enter barrel 110. The overall direction of flow of injectable fluid 180 is indicated by the solid arrow. Once a desired volume of injectable fluid 180 is drawn into barrel, filter 170 and syringe adapter are removed from syringe 100 and the filtered, injectable fluid 180 is injected by the user. This embodiment would also be applicable to the embodiment described with reference to FIG. 2.

In the embodiments shown in FIGS. 1-3, filter member 170 is removably mounted to syringe adapter 130. However, in an alternative embodiment filter member 170 and outer member 150 may be an integrally-formed or unitary structure.

Figure 4:
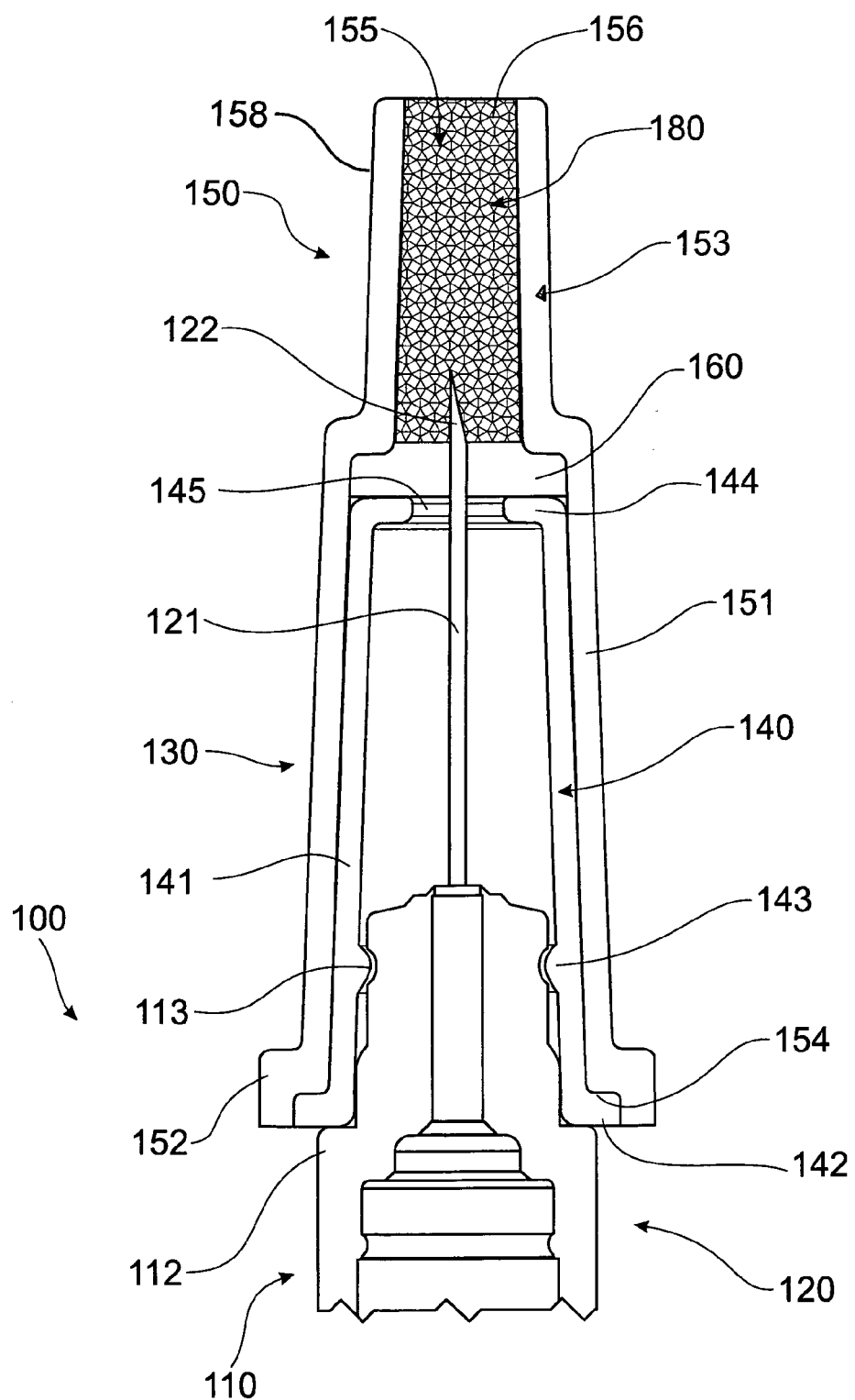
FIG. 4 is a sectional view of an embodiment of a syringe comprising a syringe adapter with filter material therein.

In another embodiment, syringe adapter 130 shown in FIG. 4, may comprise filter material 180 located inside void 155 of mounting member 153, thereby obviating the need for filter member 170. The filter material may be any material suitable for use as a syringe filter medium. Non-limiting examples include nylon, polyvinyldifluoride (PVDF), aluminium oxide (e.g. Anopore™) polytetrafluoroethylene (PTFE), polyethersulfone (PES), polypropylene, and polycarbonate filter materials, although without limitation thereto. Such filter material may be in the form of membranes, discs, particles, matrices, beds, webs and the like, as are well known in the art.

Figure 5:
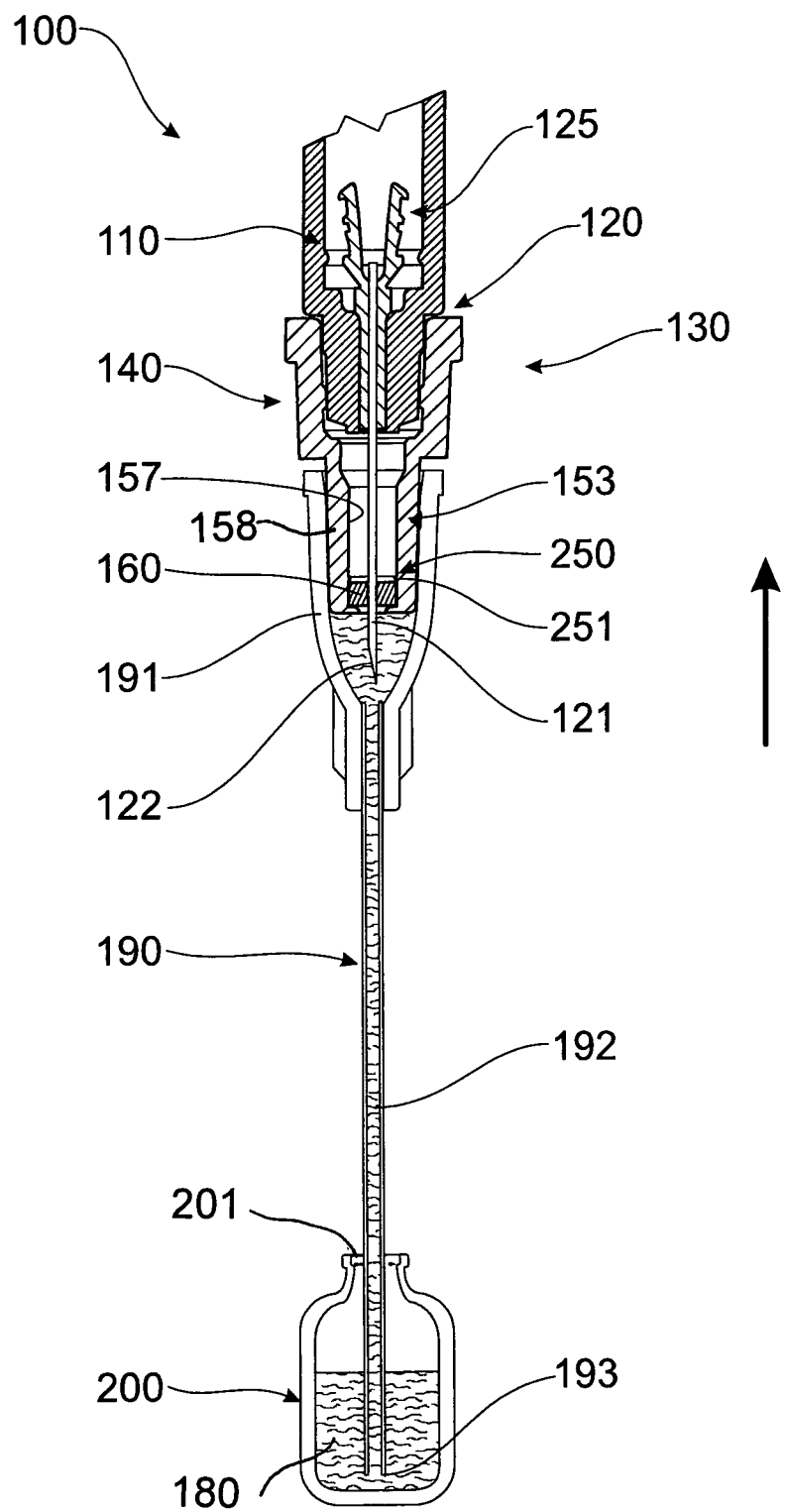
FIG. 5 is a sectional view of an embodiment of a syringe comprising a syringe adapter and filling needle removably mounted thereto.

It will also be appreciated that mounting member 153 described in FIGS. 1-4 may facilitate mounting of a needle, catheter or attachable element other than filter 170. With this in mind, an embodiment of syringe adapter 130 is shown in FIG. 5 which comprises filling needle 190 removably mounted to luer taper 158 of mounting member 153. Barrel member 140 is removably mounted to barrel 110 of retractable syringe 100. In this embodiment, retaining member 250 comprises circumferential ledge or shoulder 251 located on inside wall 157 of mounting member 153. Retaining member 250 retains sealing member 160 in place and prevents unwanted rearward movement (i.e. towards the syringe user) of sealing member 160. Retractable needle assembly 120 is essentially that described in WO2004/082747 and comprises plunger-engaging member 125 and cannula 121. In use, cannula 121 pierces sealing member 160, as in previous embodiments. Removably mounted filling needle 190 comprises base 191 and cannula 192. In use, cannula 192 pierces sealing cap 201 of container 200 and a user withdraws the syringe plunger (not shown) in the direction of the solid arrow to fill barrel 110 of syringe 100 with injectable fluid 180 from container 200. Also evident in FIG. 5 is that cannula 192 has a relatively lower gauge and/or larger bore diameter (e.g. compared to cannula 121), which is of particular assistance when injectable fluid 180 in container 200 is viscous. Cannula 192 also includes blunt tip 193 which reduces the risk of accidental needlestick injury by the user. After filling syringe 100 with fluid contents, filling needle 190 and syringe adapter 130 may be removed from syringe 100 prior to delivery of the fluid contents of the syringe 100. An advantage provided by this embodiment is that use of filling needle 190 minimizes the risk that cannula 121 of retractable needle assembly 120 is bent or burred, particularly when piercing sealing cap 201 of container 200. In this embodiment, retractable needle assembly 120 is not replaceable, so a bent or burred cannula 121 would require the entire syringe to be replaced.

It will be appreciated by persons skilled in the art that the embodiments of syringe adapter 130 shown in FIGS. 1-5 respectively comprise luer taper 158 to enable mounting of a filter 170 or filling needle 190 thereto. However, it will also be appreciated by persons skilled in the art that mounting member 153 may comprise any needle mounting or coupling system known in the art including, luer lock, luer slip, screw-threaded and/or bayonet coupling systems, although with limitation thereto.

It will be appreciated that the syringe adapter and retractable syringe described herein provides a relatively simple, easy to manufacture and use and/or cost-effective solution to adapting syringes for use with a filter. This is particularly important for improving the usefulness and broad applicability of retractable syringes with impure drugs of addition in needle exchange programs. Furthermore, this invention may make retractable syringes compliant with legal requirements imposed in certain countries by allowing filtration.

It will also be appreciated that the syringe adapter with filling needle and retractable syringe comprising same, as described herein, provides a relatively simple, easy to manufacture and use and/or cost-effective way to protect a syringe needle (e.g. a retractable needle) from damage such as bending or burring, particularly in cases where the syringe needle is not replaceable or interchangeable.

Throughout the specification, the aim has been to describe the preferred embodiments of the invention without limiting the invention to any one embodiment or specific collection of features. Various changes and modifications may be made to the embodiments described and illustrated without departing from the present invention.

The disclosure of each patent and scientific document, computer program and algorithm referred to in this specification is incorporated by reference in its entirety.

The invention claimed is:

1. A syringe adapter removably mountable to a syringe, said adapter comprising: (i) a sealing member penetrable by a needle of said syringe to facilitate filling of the syringe via the needle; and (ii) an adapter body comprising at least two members, at least one of which members is a barrel member that is capable of being mounted to a barrel of said syringe and another of which members is an outer member which comprises a mounting member that comprises a luer, wherein the barrel member and the outer member cooperate to retain the sealing member in said adapter.

2. The syringe adapter of claim 1, which comprises a filter material therein.

3. The syringe adapter of claim 1, which comprises a filter member mounted to the mounting member.

4. The syringe adapter of claim 3, wherein the filter member is removably mounted to the mounting member.

5. The syringe adapter of claim 3, wherein the filter member is integrally formed with the mounting member.

6. The syringe adapter of claim 1, wherein the mounting member comprises a filling needle removably mounted thereto.

7. The syringe adapter of claim 1 which is removably mountable to the syringe.

8. A syringe comprising the syringe adapter of claim 1 mounted thereto.

9. The syringe of claim 8, which is a retractable syringe.

10. The syringe of claim 8, wherein the syringe adapter is removably mounted thereto.

11. A method of filling the syringe of claim 8, including the step of operating the syringe to fill the syringe with fluid contents, which includes penetrating the sealing member with the needle to thereby fill the syringe via the needle.

12. The method of claim 11, which further includes the step of mounting the syringe adapter to the retractable syringe before operating the syringe to fill the syringe with fluid contents.

13. The method of claim 12, further including the step of removing the syringe adapter from the retractable syringe after operating the syringe to fill the syringe with fluid contents.

14. The method of claim 11, wherein the adapter comprises a filter member that filters the fluid contents when filling the syringe with the fluid contents.

15. The method of claim 11, wherein the syringe adapter comprises a filling needle mounted thereto.

16. The adapter of claim 1, wherein the mounting member comprises a substantially frustoconical body and a base flange that releasably engages the barrel.

17. The adapter of claim 1 wherein the outer member comprises an inner circumferential shoulder that co-operates with a crown of said mounting member to retain said sealing member in place in said adapter.

* * * * *